United States Patent
Kim et al.

(10) Patent No.: US 10,682,465 B2
(45) Date of Patent: Jun. 16, 2020

(54) COVER BODY AND MEDICINAL FLUID INJECTION DEVICE HAVING SAME

(71) Applicant: EOFLOW CO., LTD., Seongnam-si Gyeonggi-do (KR)

(72) Inventors: Seung Ha Kim, Goyang-si (KR); Jong Ook Jeong, Seongnam-si (KR); Jesse Jaejin Kim, Seongnam-si (KR)

(73) Assignee: EOFlow Co., Ltd., Seongnam-si (KR)

( * ) Notice: Subject to any disclaimer, the term of this patent is extended or adjusted under 35 U.S.C. 154(b) by 0 days.

(21) Appl. No.: 16/080,651

(22) PCT Filed: Feb. 24, 2017

(86) PCT No.: PCT/KR2017/002036
§ 371 (c)(1),
(2) Date: Aug. 28, 2018

(87) PCT Pub. No.: WO2017/150845
PCT Pub. Date: Sep. 8, 2017

(65) Prior Publication Data
US 2019/0091408 A1   Mar. 28, 2019

(30) Foreign Application Priority Data
Feb. 29, 2016   (KR) .................. 10-2016-0024677

(51) Int. Cl.
*A61M 5/31*   (2006.01)
*A61M 5/20*   (2006.01)
(Continued)

(52) U.S. Cl.
CPC ............ *A61M 5/3146* (2013.01); *A61M 5/20* (2013.01); *A61M 5/31* (2013.01); *A61M 5/32* (2013.01);
(Continued)

(58) Field of Classification Search
CPC ........ A61M 5/3146; A61M 5/20; A61M 5/34; A61M 2005/14264
(Continued)

(56) References Cited

U.S. PATENT DOCUMENTS

| 4,775,376 A | 10/1988 | Strung |
| 7,785,288 B2 | 8/2010 | Mernoe et al. |
| 2016/0243317 A1* | 8/2016 | Asano .................... A61M 5/36 |

FOREIGN PATENT DOCUMENTS

| EP | 0 252 644 A2 | 1/1988 |
| JP | S63-24955 A | 2/1988 |

(Continued)

OTHER PUBLICATIONS

Office Action dated Jul. 9, 2019 in Japanese Patent Application No. 2018-564714; 3 pages.
(Continued)

*Primary Examiner* — Phillip A Gray
(74) *Attorney, Agent, or Firm* — Knobbe, Martens, Olson & Bear, LLP

(57) ABSTRACT

The disclosed technology relates to medicinal fluid injection devices. In one aspect, a medicinal fluid injection device includes a housing having an opening in a side surface thereof, a storage container arranged inside the housing and configured to store a medicinal fluid, an injection needle connected to the storage container and configured to inject the medicinal fluid when stored in the storage container through the opening, and a cover body covering the opening, wherein the cover body includes a cover part configured such that the shape of the cover part changes according to air pressure caused by the injection needle.

5 Claims, 10 Drawing Sheets

(51) Int. Cl.
*A61M 5/32* (2006.01)
*A61M 5/34* (2006.01)
*A61M 5/142* (2006.01)

(52) U.S. Cl.
CPC ............ *A61M 5/34* (2013.01); *A61M 5/14248* (2013.01); *A61M 5/3213* (2013.01); *A61M 2005/14264* (2013.01)

(58) Field of Classification Search
USPC ........................................................ 604/181
See application file for complete search history.

(56) References Cited

FOREIGN PATENT DOCUMENTS

| | | |
|---|---|---|
| JP | 2000-354627 A | 12/2000 |
| JP | 2006-511263 A | 4/2006 |
| JP | 2006-180904 | 7/2006 |
| JP | 2013-504403 | 2/2013 |
| JP | 2014-236906 | 12/2014 |
| KR | 10-2009-0018645 | 2/2009 |
| KR | 10-2011-0059637 | 6/2011 |
| KR | 10-2014-0140747 | 12/2014 |
| WO | WO 2005/011779 A1 | 2/2005 |
| WO | WO 2009/106517 A1 | 9/2009 |
| WO | WO 2015/081337 A2 | 6/2015 |
| WO | WO 2015/123095 A1 | 8/2015 |

OTHER PUBLICATIONS

Office Action dated Jan. 10, 2017 in Korean Patent Application No. 10-2016-0024677; 7 pages.
International Search Report dated Jun. 5, 2017 in PCT Application No. PCT/KR2017/002036; 2 pages.
Extended Search Report dated Aug. 30, 2019 in European Patent Application No. 17760249.7; 12 pages.

* cited by examiner

COVER BODY AND MEDICINAL FLUID INJECTION DEVICE HAVING SAME

TECHNICAL FIELD

The present disclosure relates to a device for finely injecting a medicinal fluid such as insulin and a cover body for use in the device.

BACKGROUND ART

Diabetes is a medical condition based on metabolic disorders caused by lack of insulin, which is one of the hormones produced by the pancreas. A diabetic patient has to use a method of injecting insulin into his/her body as one of the aggressive methods. An insulin injection device may be used to appropriately inject insulin into the body according to a change in a patient's blood glucose.

A medicinal fluid injection device such as an insulin injection device may be semi-permanently used while constantly replenishing a medicinal fluid therein. In such a case, foreign materials (e.g., air), other than the medicinal fluid, need to be prevented from being injected through an injection needle into the body or the medicinal fluid injection device needs to be prevented from being contaminated.

SUMMARY OF CERTAIN INVENTIVE ASPECTS

Provided are a cover body capable of preventing internal contamination of a device and undergoing a deformation due to air discharged through an injection needle and a medicinal fluid injection device having the cover body.

According to an aspect of the present disclosure, a medicinal fluid injection device includes a housing having an opening in a side surface thereof; a storage container arranged inside the housing and storing a medicinal fluid; an injection needle connected to the storage container and injecting the medicinal fluid through the opening; and a cover body covering the opening, wherein the cover body includes a cover part of which a shape changes according to an air pressure caused by the injection needle.

At least one region of the cover part may bulge in a direction away from the housing due to the air pressure.

The cover part may include an elastic material.

The elastic material may include a polymer.

The cover part may include a corrugation in a thickness direction of the cover part.

The at least one region of the cover part may be thinner than a peripheral region around the at least one region.

The cover body may further include a frame, the frame including a hole corresponding to the opening of the housing.

The frame may further include a sleeve protruding toward the cover part and combined with the cover part.

The cover body may further include an auxiliary cover part positioned opposite the cover part with the hole between the auxiliary cover part and the cover part.

The auxiliary cover part may include a polymer.

The medicinal fluid injection device may further include a shape that is concave in a direction toward the cover part to accommodate an initial medicinal fluid discharged from the injection needle penetrating through the auxiliary cover part.

According to another aspect of the present disclosure, a cover body for a medicinal fluid injection device includes a frame having a hole and a cover part combined with the frame, wherein a shape of the cover part changes with a change in an air pressure around the cover part.

The cover part may include an elastic material.

The elastic material may include a polymer.

The cover part may include a corrugation in a thickness direction of the cover part.

At least one region of the cover part may be thinner than a peripheral region around the at least one region.

The cover body may further include an auxiliary cover part positioned opposite the cover part with the hole between the auxiliary cover part and the cover part.

A space between the cover part and the auxiliary cover part may be a closed space fluidically separated from outside.

The auxiliary cover part may have a shape that is concave in a direction toward the cover part.

The auxiliary cover part may include a polymer.

Other aspects, features, and advantages than those described above will be clear from the accompanying drawings, the claims, and the descriptions of embodiments below.

According to embodiments of the present disclosure, a cover body and a medicinal fluid injection device having the same prevent the backflow of air during a priming operation for removing air from an injection needle and prevent device contamination. The scope of the present disclosure is not limited by these effects.

DETAILED DESCRIPTION OF CERTAIN ILLUSTRATIVE EMBODIMENTS

Figure 1:
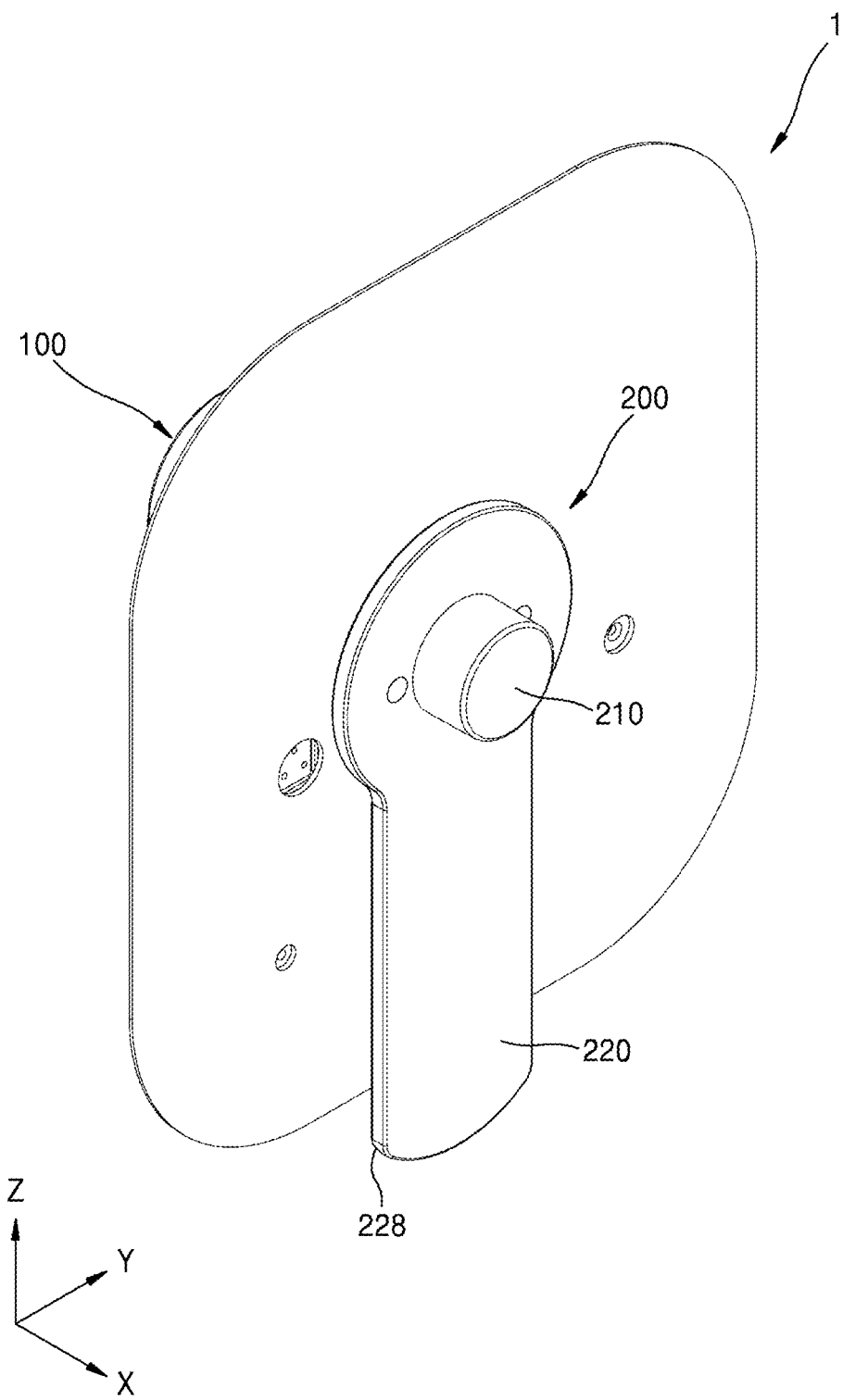
FIG. 1 is a schematic perspective view of a medicinal fluid injection device according to an embodiment of the present disclosure.

The present disclosure may include various modifications and different embodiments. In this regard, specific embodiments are illustrated in the drawings and will be described in detail. Advantageous effects, features, and methods for achieving the effects and features will become more apparent by explaining the embodiments in detail with reference to the accompanying drawings. However, the present disclosure is not limited to these embodiments but may be implemented in various modes.

The embodiments of the present disclosure will now be described in detail with reference to the accompanying drawings, in which like reference numerals denote like elements, and thus their description will be omitted.

The terms first, second, etc. are used in the description of the embodiments to only distinguish one element from another.

As used herein, the singular forms "a", "an" and "the" are intended to include the plural forms as well, unless the context clearly indicates otherwise.

It will be further understood that the terms "comprises" and/or "comprising," or "includes" and/or "including" when used in this specification, specify the presence of stated features or components, but do not preclude the presence or addition of one or more other features or components.

In the drawings, the size of elements may be exaggerated or reduced for clarity. For instance, the size and thickness of each element may be arbitrarily illustrated in the drawings, and therefore, the present disclosure is not limited to the drawings.

It will be understood that when a region or an element is referred to as being "connected" to another region or element, it can be directly connected to the other region or element, or intervening regions or elements may be present.

Figure 2:
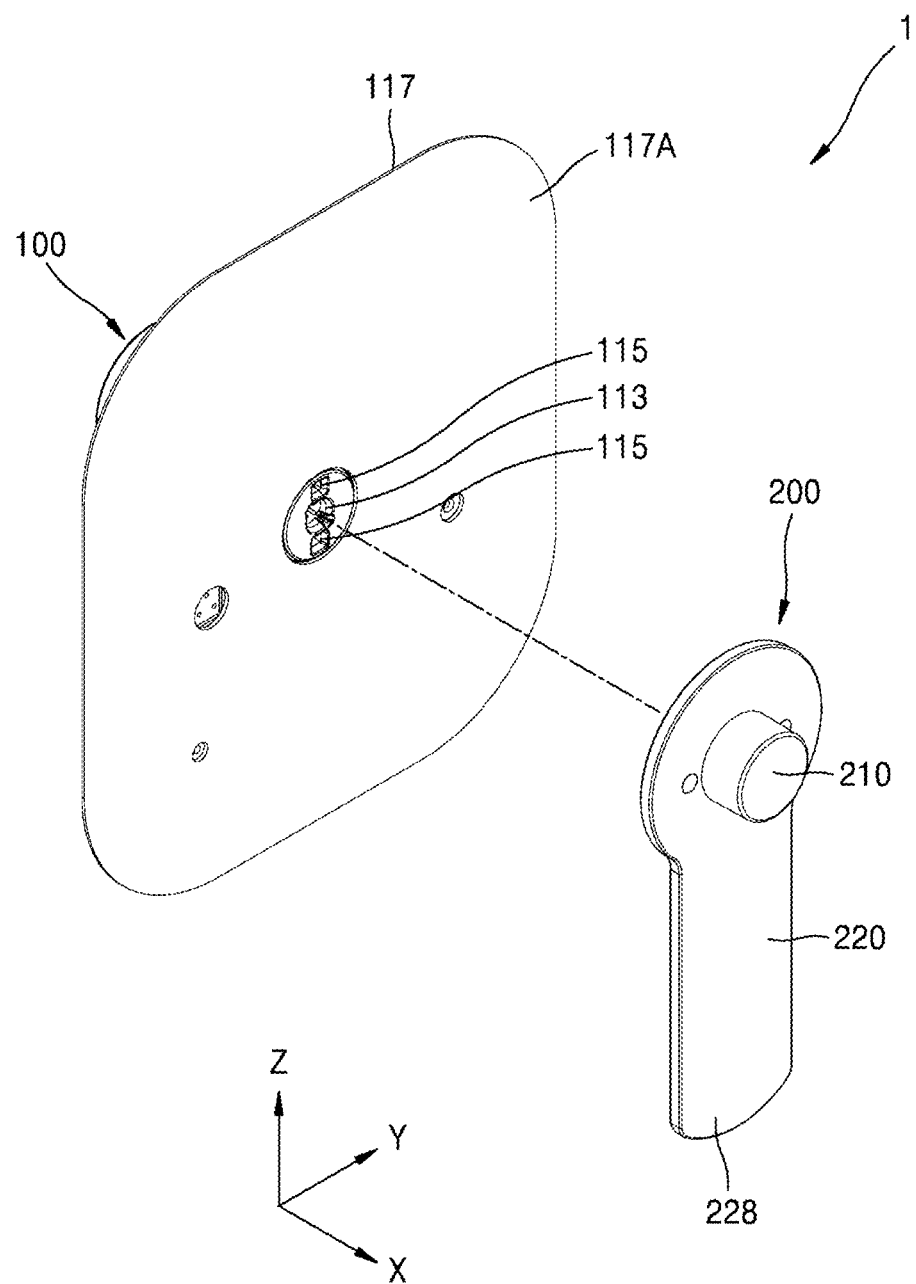
FIG. 2 is an exploded perspective view of FIG. 1.
Figure 3:
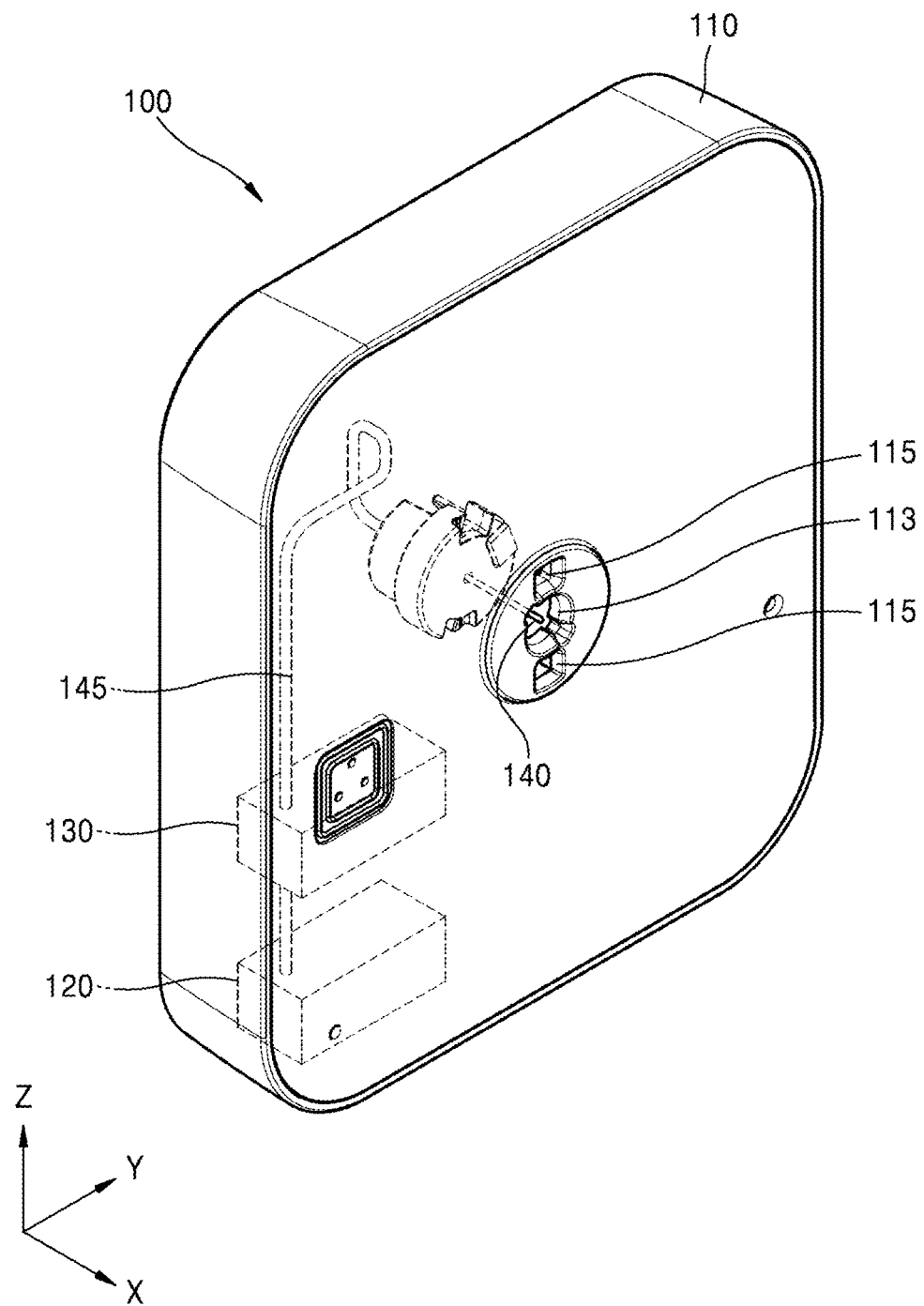
FIG. 3 is a schematic perspective view of a main body according to an embodiment of the present disclosure.

FIG. 1 is a schematic perspective view of a medicinal fluid injection device according to an embodiment of the present disclosure. FIG. 2 is an exploded perspective view of FIG. 1. FIG. 3 is a schematic perspective view of a portion of a main body according to an embodiment of the present disclosure. For convenience of description, a patch plate 117 of FIG. 2 is omitted in FIG. 3.

Referring to FIGS. 1 through 3, a medicinal fluid injection device 1 may include a main body 100 and a cover body 200. The main body 100 may include a housing 110 having an opening 113 in a side surface, a storage container 120 arranged inside the housing 110, a pump 130, and an injection needle 140 connected to the storage container 120 through the pump 130.

The housing 110 may include a material such as plastic or a metallic material. The opening 113 may be formed in the side surface of the housing 110. The opening 113 may be located at the center of the side surface of the housing 110 in FIG. 1, but the present disclosure is not limited thereto.

The housing 110 may include the patch plate 117 provided on the side surface of the housing 110 in which the opening 113 is formed. The patch plate 117 may have an adhesive surface 117A which allows the medicinal fluid injection device 1 to be attached to a patient's skin surface. The adhesive surface 117A may be protected by release paper (not shown). The release paper may be removed from the adhesive surface 117A when the medicinal fluid injection device 1 needs to be fixed to the patient's skin surface via the adhesive surface 117A.

The storage container 120 may store and hold as much medicinal fluid as necessary to be injected several times to several tens of times. When the medicinal fluid stored in the storage container 120 is all consumed, the storage container 120 may be newly filled with a new medicinal fluid.

The pump 130 may be a small size pump, e.g., a micropump, and may pump a predetermined amount of the medicinal fluid. In an embodiment, the pump 130 may pump several tens of nanoliters to several microliters of the medicinal fluid at a flow rate of several microliters to several tens of microliters per minute, but the present disclosure is not limited thereto.

The injection needle 140 may be connected to the storage container 120 through a tube 145. The pump 130 may be positioned along a path between the storage container 120 and the injection needle 140. The medicinal fluid in the storage container 120 may be moved by the pump 130 to the injection needle 140 through the tube 145. When a button (not shown) in the main body 100 is pushed, the injection needle 140 protrudes outward through the opening 113 of the main body 100 under the control of a controller (not shown). Thus, the medicinal fluid may be injected into a patient through the injection needle 140.

The cover body 200 may cover the opening 113 of the main body 100. The cover body 200 may be coupled to a recess 115 formed in the side surface of the housing 110 and may be configured to be easily detachable using a handle 228.

The cover body 200 may include a part that may include an elastic material. Thus, a shape of the portion of the cover body 200 may be changed by an air pressure inside the cover body 200 facing the main body 100. In an embodiment, a shape of a cover part 210 of the cover body 200 may be changed by an air pressure around the cover part 210, e.g., an air pressure from the inside of the cover part 210. In an embodiment, at least one region of the cover part 210 may bulge in a direction (e.g., an X direction) away from the housing 110. The cover part 210 may be combined with a frame 220 which supports the cover part 210.

The cover body 200 will be described further below.

Figure 4:
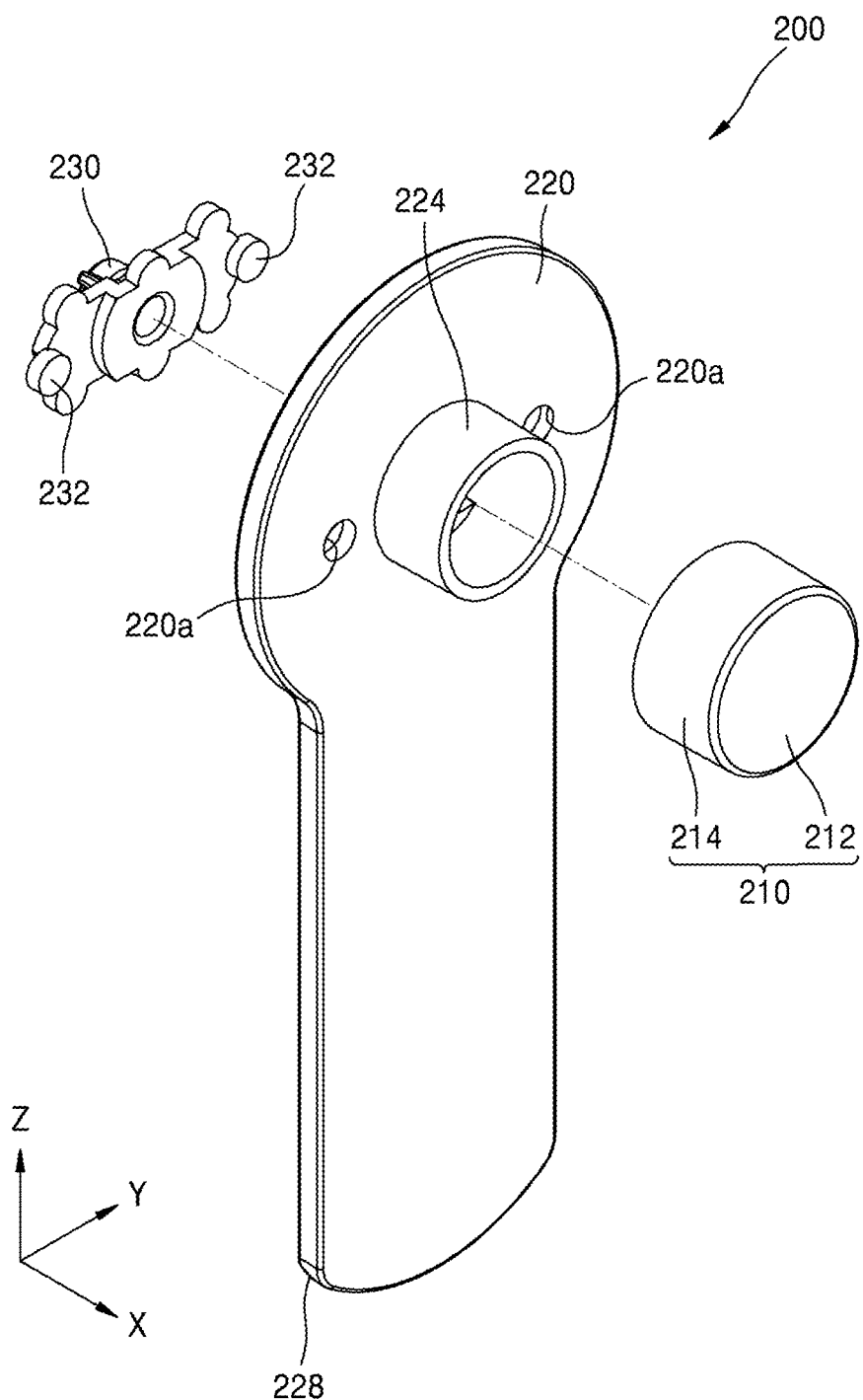
FIGS. 4 and 5 are schematic exploded perspective views of a cover body according to an embodiment of the present disclosure.
Figure 5:
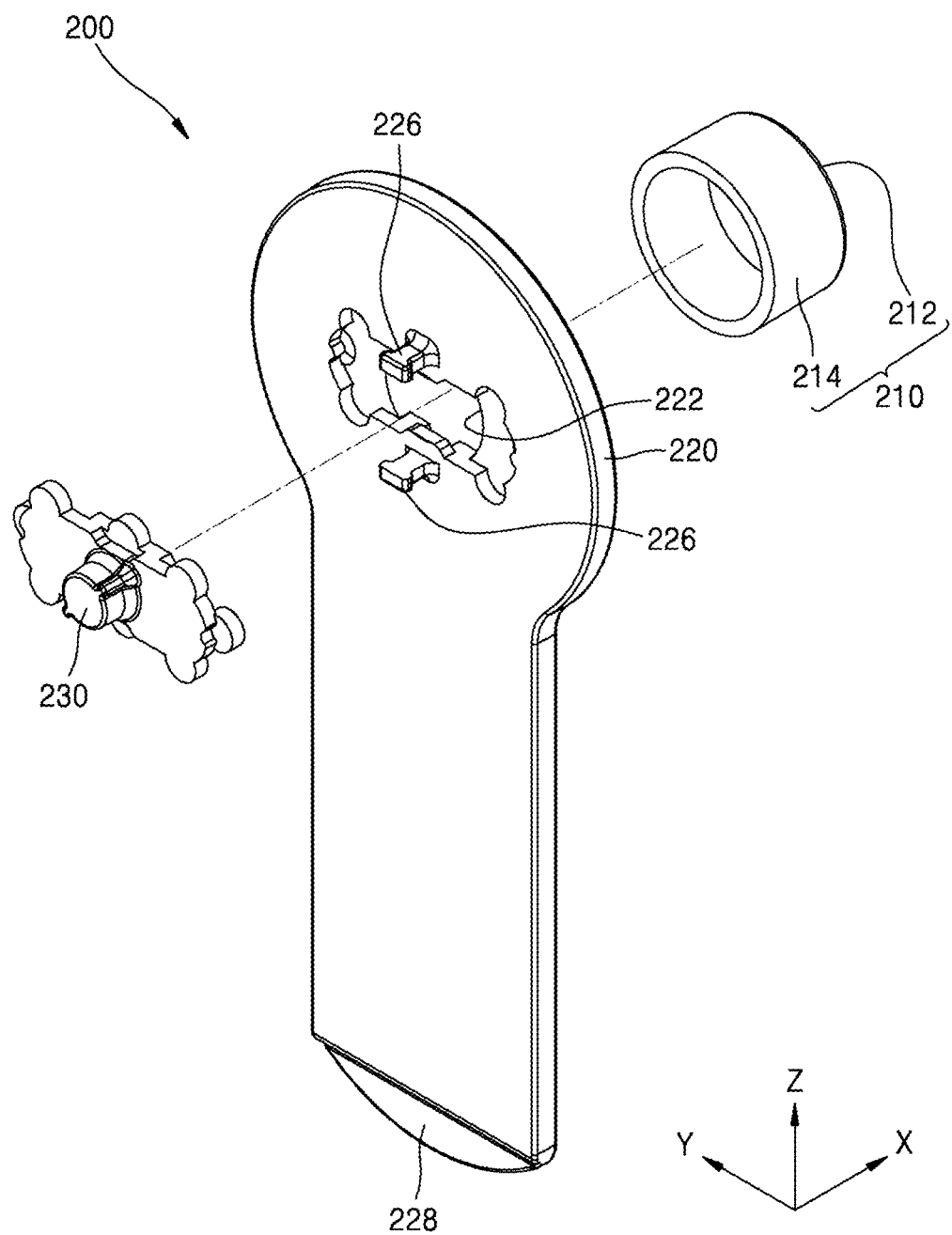
Figure 6:
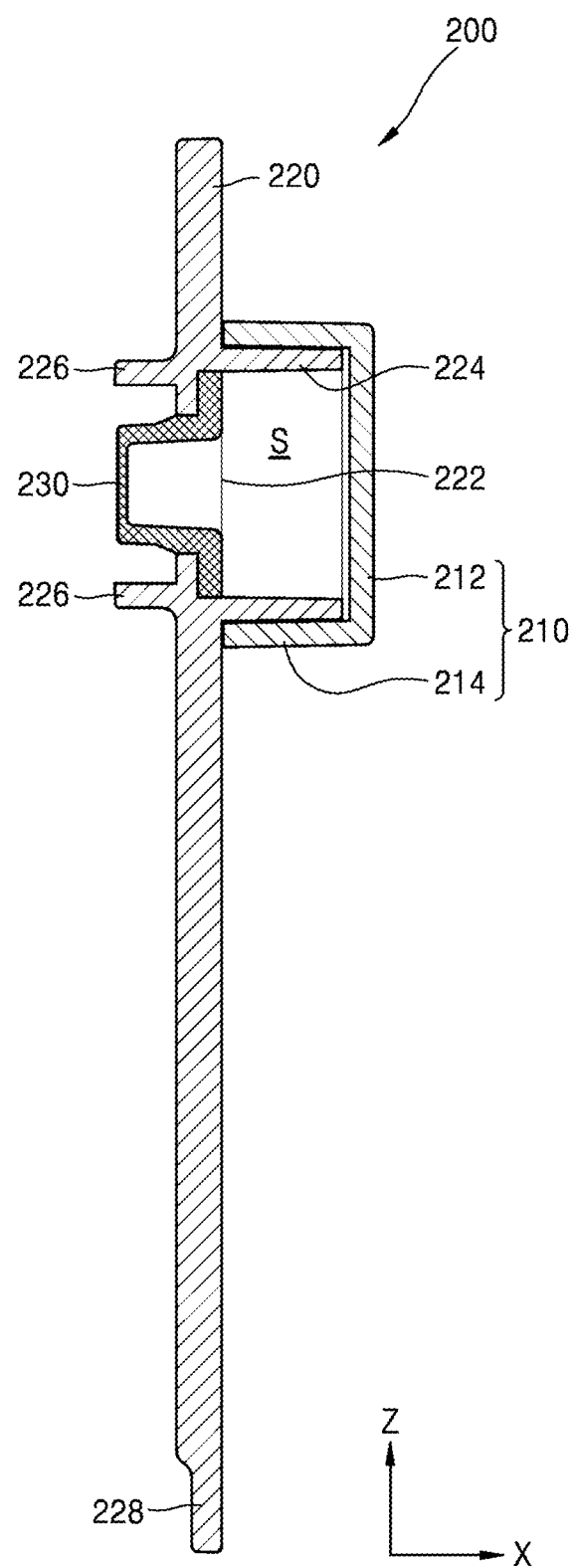
FIG. 6 is a cross-sectional view of a cover body according to an embodiment of the present disclosure.

FIGS. 4 and 5 are each schematic exploded perspective views of a cover body according to an embodiment of the present disclosure. FIG. 6 is a cross-sectional view of a cover body according to an embodiment of the present disclosure.

Referring to FIGS. 4 through 6, the cover part 210 may be connected to the frame 220 at a side of the frame 220, and an auxiliary cover part 230 may be connected to the frame 220 at an opposite side of the frame 220.

The cover part 210 may include an elastic material. In an embodiment, the cover part 210 may include a polymer. The polymer may include natural rubber, synthetic rubber, or a silicone-based polymer. The silicone-based polymer may include polydimethylsiloxane (PDMS) or hexamethyldisiloxane (HMDSO). In another embodiment, the elastic material may include various materials such as polyurethane and polyurethane acrylate.

The cover part 210 may include a front portion 212 and a lateral portion 214 around the front portion 212. In an embodiment, the front portion 212 and the lateral portion 214 may be integrally formed with each other from one material.

The frame 220 may include a hole 222. The hole 222 may correspond to the opening 113 of the main body 100 and penetrate the frame 220. The frame 220 may include a sleeve 224 at a side (hereinafter, referred to as a first side surface) facing the cover part 210 and a protrusion 226 at an opposite side (hereinafter, referred to as a second side surface) facing the main body 100.

The sleeve 224 may protrude from the frame 220 in the X direction. The sleeve 224 may be a structure to be combined with the cover part 210. The lateral portion 214 of the cover part 210 may be combined with the sleeve 224 so that the cover part 210 may be connected to the frame 220.

The protrusion 226 may protrude in a direction opposite the sleeve 224. As a structure for a combination with the main body 100, the protrusion 226 may be inserted into the recess 115 (see FIG. 2) provided in the housing 110 of the main body 100. The frame 220 may include the handle 228 extending along a side thereof. When the cover body 200 needs to be removed to inject the medicinal fluid into a patient, the cover body 200 may be easily detached from the main body 100 using the handle 228.

The auxiliary cover part 230 may be positioned opposite the cover part 210 with the hole 222 of the frame 220 between the auxiliary cover part 230 and the cover part 210. The auxiliary cover part 230 may be connected to the frame 220 when a coupling protrusion 232 is inserted and locked into a coupling hole 220a formed in the frame 220.

The auxiliary cover part 230, as described below with reference to FIGS. 7A and 7B, may include a polymer material such that the injection needle 140 may penetrate through the auxiliary cover part 230. The auxiliary cover part 230 may be convex in a direction facing the main body 100, i.e., concave in a direction (i.e., the X direction) facing the cover part 210.

Due to the cover part 210 and the auxiliary cover part 230, which are connected to the frame 220 at opposite sides of the frame 220 with the hole 222 between the cover part 210 and the auxiliary cover part 230, a space S is formed between the cover part 210 and the auxiliary cover part 230. Although the space S is a closed space, as shown in FIG. 7A, the space S may be fluidically connected to the injection needle 140 as the injection needle 140 penetrates through the auxiliary cover part 230, as described below with reference to FIG. 7B.

Figure 7A:
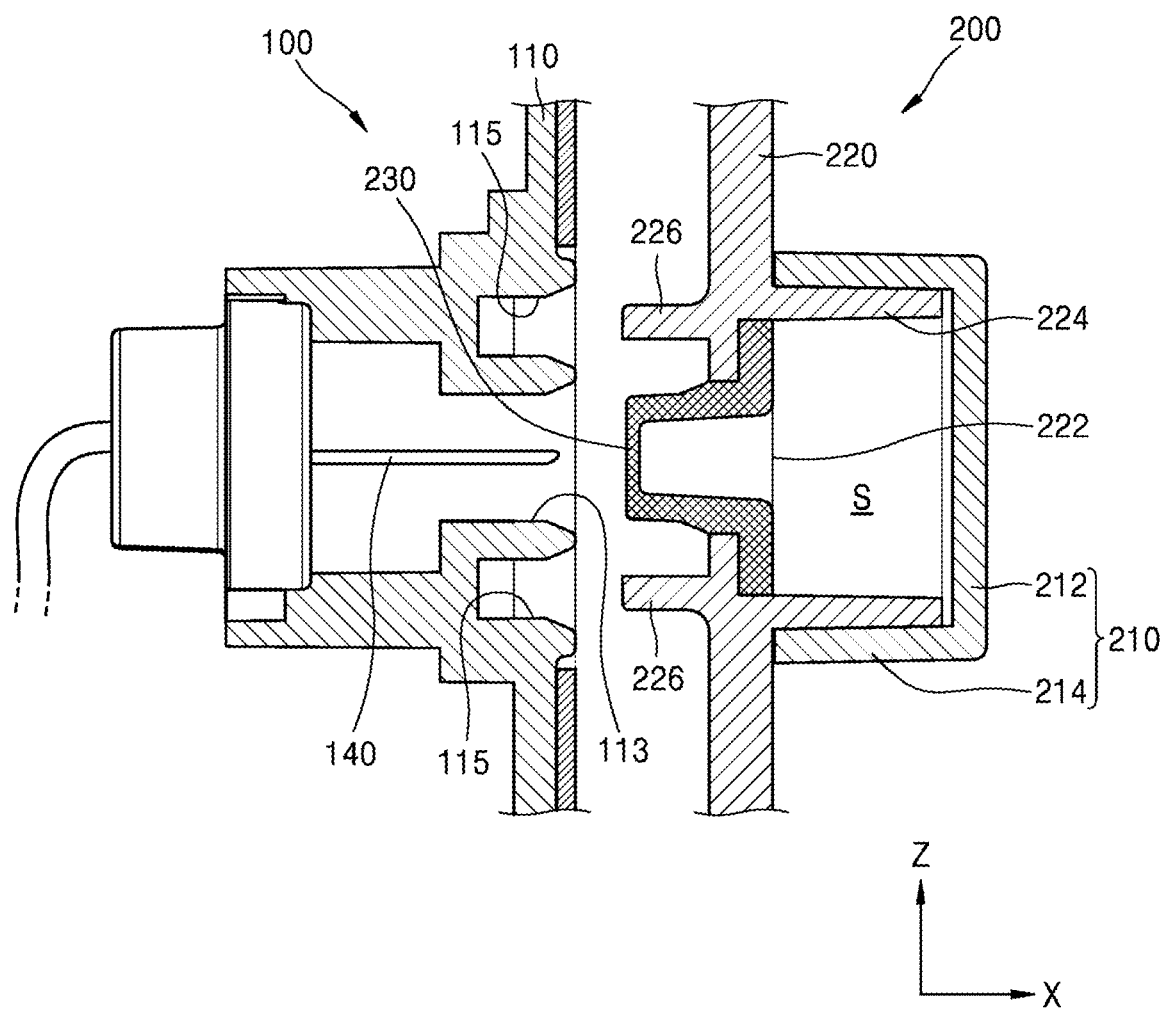
FIGS. 7A and 7B are respectively cross-sectional views of a cover body and a main body before and after being combined with each other.
Figure 7B:
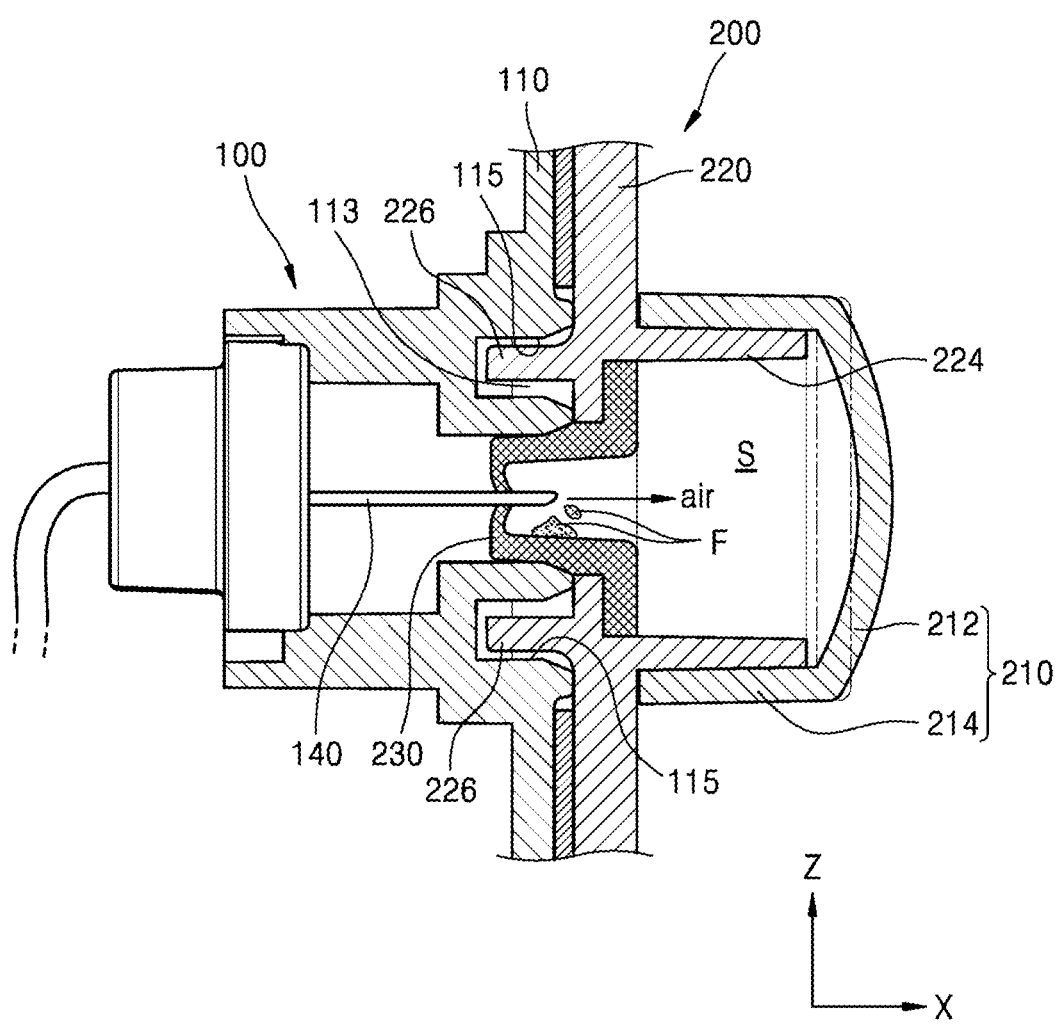

FIGS. 7A and 7B are respectively cross-sectional views of a cover body and a main body before and after being combined with each other.

Referring to FIGS. 7A and 7B, the cover body 200 is positioned to cover the opening 113 of the main body 100, and the protrusion 226 of the cover body 200 is inserted into the recess 115. In an embodiment, when the cover body 200 is combined with the main body 100, the injection needle 140 in the opening 113 may penetrate through the auxiliary cover part 230 of the cover body 200.

For injection of the medicinal fluid, the cover body 200 is detached from the main body 100, and the medicinal fluid in the storage container 120 is injected into a patient through the injection needle 140 according to an operation of the pump 130, as described above with reference to FIGS. 1 through 3.

When air is in the injection needle 140 before the medicinal fluid is injected, there is a risk that the air may be injected into a patient, and therefore, an operation of removing the air, e.g., a priming operation, is performed. For example, the medicinal fluid is moved by the pump 130 (see FIG. 3) which operates according to a signal of the controller. The air in the injection needle 140 may be discharged by the movement of the medicinal fluid as shown in FIG. 7B. The discharged air stays in the space S. At this time, a shape of the cover part 210 changes due to the pressure of the discharged air, thereby the cover part 210 bulging outward.

In a comparative example, when the cover part 210 includes a nonelastic material, e.g., reinforced plastic, a shape of the cover part 210 does not change. In this case, even when the air is discharged from the injection needle 140, the space S has no margin to accommodate the discharged air, and therefore, the air flows backward into the injection needle 140 and may be injected into a patient. However, according to embodiments of the present disclosure, the shape of the cover part 210 changes due to the pressure of the air discharged from the injection needle 140, and therefore, the problem described above may be prevented.

During the priming operation, a little medicinal fluid F may be discharged together with the air. The little medicinal fluid F may gather in the auxiliary cover part 230 having a shape that is concave in a direction (e.g., the X direction) in which medicinal fluid is discharged. Since the little medicinal fluid F is in the space S of the cover body 200, the inside of the main body 100 may be prevented from being contaminated by the little medicinal fluid F.

In the embodiments described above with reference to FIGS. 7A and 7B, the injection needle 140 penetrates through the auxiliary cover part 230 when the cover body 200 is combined with the main body 100, but the present disclosure is not limited thereto. In other embodiments, the injection needle 140 may be positioned further inside than a position shown in FIG. 7A, and when the priming operation is necessary, the injection needle 140 may be moved by the operation of the controller to penetrate through the auxiliary cover part 230, as shown in FIG. 7B.

Figure 8:
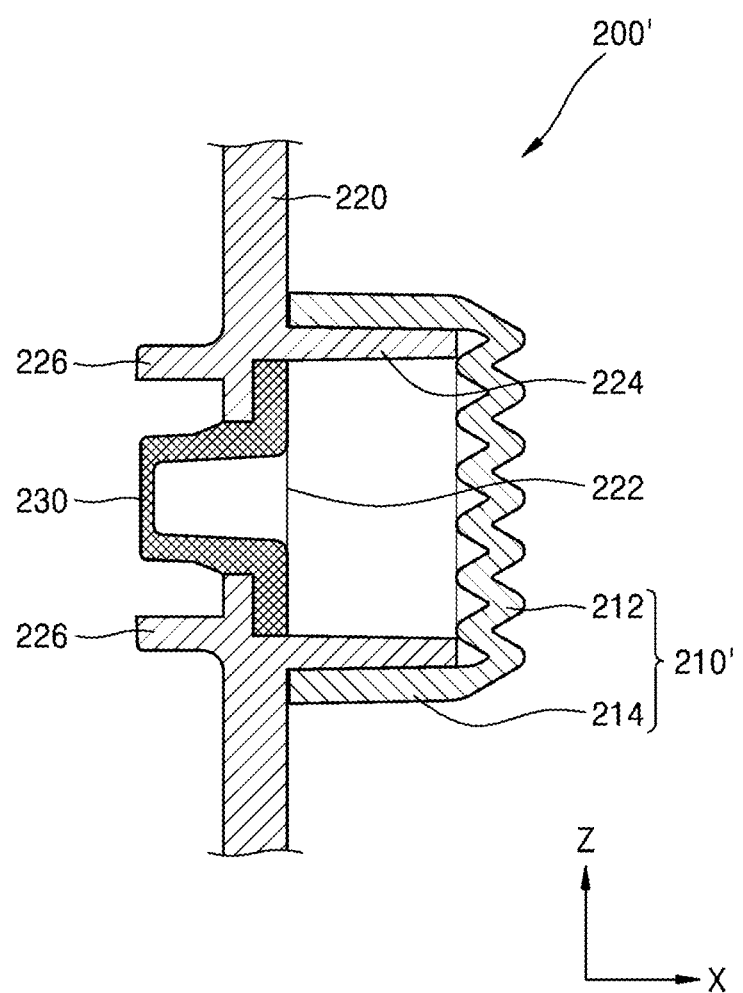
FIGS. 8 and 9 are respectively cross-sectional views of cover bodies according to embodiments of the present disclosure.
Figure 9:
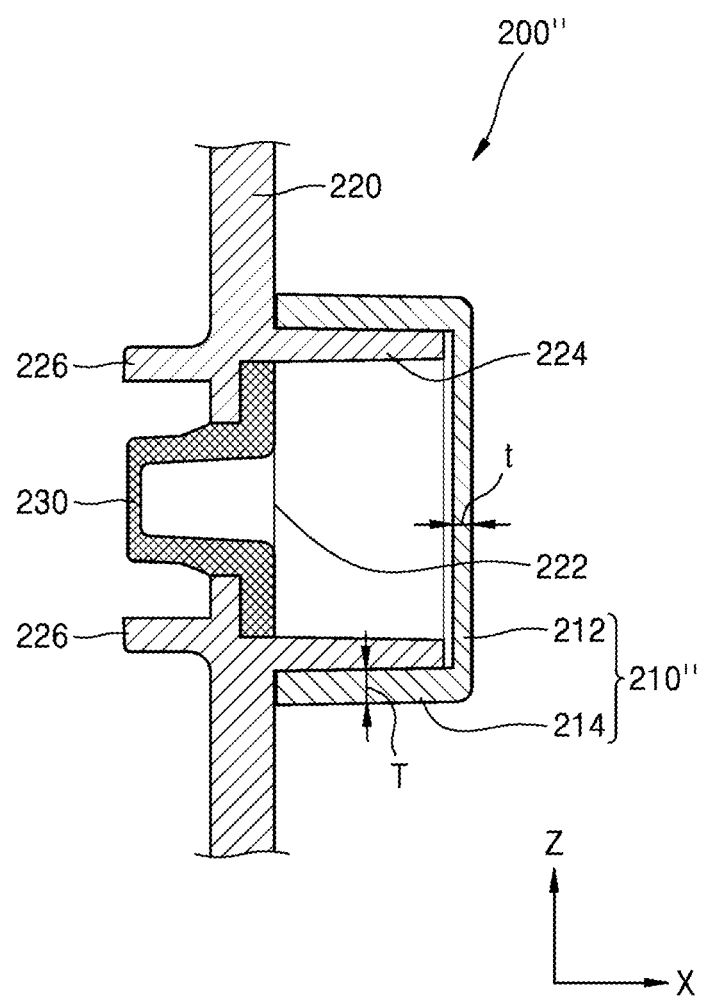

FIGS. 8 and 9 are respectively cross-sectional views of cover bodies according to different embodiments of the present disclosure.

Referring to FIG. 8, a cover body 200' has a similar structure to the cover body 200. Thus, redundant descriptions will be omitted and descriptions will be focused on the differences between the cover bodies 200 and 200'.

A cover part 210' in FIG. 8 may have corrugations. In an embodiment, the front portion 212 may have a corrugated shape in a thickness direction. Since the front portion 212 has corrugations, the shape of the cover part 210' may be easily changed by air discharged from the injection needle 140 during a priming operation. In an embodiment, the cover part 210' may include the elastic material described above. In another embodiment, the cover part 210' may include a non-elastic material since the cover part 210' has corrugations.

Referring to FIG. 8, although corrugations are formed throughout the front portion 212, the present disclosure is not limited thereto. The front portion 212 may be partially corrugated.

Referring to FIG. 9, a cover body 200" has the similar structure to the cover body 200. Thus, redundant descriptions will be omitted, and descriptions will be focused on the differences between the cover bodies 200 and 200".

A cover part 210" in FIG. 9 may have different thicknesses in different portions. In an embodiment, a thickness "t" of the front portion 212 may be less than a thickness T of the lateral portion 214. Accordingly, the shape of the cover part 210" may be easily changed by the pressure of air discharged during a priming operation. The cover part 210" may include the elastic material described above.

Although the front portion 212 has the uniform thickness "t" (where t<T) in FIG. 9, the present disclosure is not limited thereto. In another embodiment, a thickness of at least one region of the front portion 212 may be less than the thickness T of the lateral portion 214.

While the present disclosure has been described with reference to embodiments shown in the drawings, it will be understood by those skilled in the art that the embodiments are just exemplary and various changes in form and details may be made therein. Therefore, the scope of the present disclosure will be defined by the technical ideas of the appended claims.

The invention claimed is:

1. A medicinal fluid injection device comprising:
a housing having an opening in a side surface thereof;
a storage container arranged inside the housing and configured to store a medicinal fluid;
an injection needle connected to the storage container and configured to inject the medicinal fluid when stored in the storage container through the opening;
a pump arranged inside the housing;
a frame coupled to the housing and having a hole corresponding to the opening;
a cover part positioned on a side of the frame; and an auxiliary cover part positioned opposite the cover part with the hole between the auxiliary cover part and the cover part, wherein a space is formed between the cover part and the auxiliary cover part, the space configured to be fluidly connected to the injection needle as the injection needle passes through the auxiliary cover part, and wherein the medicinal fluid injection device is configured such that air in the injection needle is discharged toward the space by a movement of the medical fluid caused by the pump.

2. The medicinal fluid injection device of claim 1, wherein at least one region of the cover part bulges in a direction away from the housing due to air pressure caused by air discharged through the injection needle.

3. The medicinal fluid injection device of claim 1, wherein the cover part comprises a polymer.

4. The medicinal fluid injection device of claim 1, wherein the frame further comprises a sleeve protruding toward the cover part and combined with the cover part.

5. The medicinal fluid injection device of claim 1, wherein the auxiliary cover part comprises a polymer.

\* \* \* \* \*

UNITED STATES PATENT AND TRADEMARK OFFICE
CERTIFICATE OF CORRECTION

PATENT NO. : 10,682,465 B2
APPLICATION NO. : 16/080651
DATED : June 16, 2020
INVENTOR(S) : Seung Ha Kim et al.

Page 1 of 1

It is certified that error appears in the above-identified patent and that said Letters Patent is hereby corrected as shown below:

On the Title Page

Column 1, Item (72), Lines 1-2, under Inventors, after "Seung Ha Kim, Goyang-si (KR);" delete "Jong Ook Jeong, Seongnam-si (KR);".

Signed and Sealed this
First Day of December, 2020

Andrei Iancu
*Director of the United States Patent and Trademark Office*